United States Patent [19]

Way et al.

[11] Patent Number: 5,325,066

[45] Date of Patent: Jun. 28, 1994

[54] DENSITY COMPENSATED PIPELINE MONITOR

[75] Inventors: Dennis K. Way, Calgary; Lawrence D. Neumeister, Edmonton, both of Canada

[73] Assignee: Spartan Controls Ltd., Calgary, Canada

[21] Appl. No.: 914,593

[22] Filed: Jul. 20, 1992

[51] Int. Cl.$^5$ .................... G01N 27/22; G01R 27/26
[52] U.S. Cl. .................... 324/664; 324/669; 324/689; 73/61.43; 73/861.01; 73/861.02
[58] Field of Search .............. 324/663, 664, 669, 670, 324/689; 73/61.43, 61.41, 861.01, 861.02, 861.08, 861.14

[56] References Cited

U.S. PATENT DOCUMENTS

| | | | |
|---|---|---|---|
| 3,546,926 | 12/1970 | Dunavent, Jr. et al. | 324/669 |
| 4,359,638 | 11/1982 | Allport | 324/669 |
| 4,441,362 | 4/1984 | Carlson | 73/155 |
| 4,458,524 | 7/1984 | Meador et al. | 73/61.1 R |
| 4,543,191 | 9/1985 | Stewart et al. | 73/61.41 |
| 4,751,842 | 6/1988 | Ekrann et al. | 324/663 |
| 5,033,289 | 7/1991 | Cox | 73/61.1 R |

OTHER PUBLICATIONS

Brochure entitled "BS & W Monitor, Model SC1000" published by the applicant, Spartan Controls Ltd. of Calgary and Edmonton, Alberta, Canada, Mar. 1988, pp. 1-4.

Primary Examiner—Kenneth A. Wieder
Assistant Examiner—Chris Tobin
Attorney, Agent, or Firm—John R. Uren

[57] ABSTRACT

Apparatus and method for determining the water content of an oil and water mixture such as is transported by pipelines and which oil and water may vary in density from time to time. A densitometer measures the density of the oil and water mixture in the pipeline and a value for the dielectric constant of the oil is obtained from the density measurement by correlating the density reading with a capacitance or dielectric constant reading from an empirically generated chart. A basal sediment and water instrument measures the dielectric constant of the same mixture. The difference between the two dielectric constants is then obtained. This result is converted directly into a water based percentage by volume of the oil-water mixture being carried by the pipeline.

5 Claims, 6 Drawing Sheets

DENSITY COMPENSATED PIPELINE MONITOR

INTRODUCTION

This invention relates to a cut monitor and, more particularly, to a cut monitor which utilises density compensation to obtain the water content of a hydrocarbon liquid and water mixture.

BACKGROUND OF THE INVENTION

It is necessary in many applications to obtain an indication of the water content of a hydrocarbon liquid and water mixture such as a petroleum and water mixture. For example, pipeline operators will ordinarily wish to ensure that the oil carried by such pipelines has a water content which does not exceed a certain value. This is so because the pipeline companies wish to ensure they are not purchasing water and paying for oil. This is also so because water can corrode the pipeline which can result in premature pipeline failure. Water can also freeze in the pipeline and block flow. This has the potential to close the pipeline and shut in the oil being carried by the pipeline.

The maximum amount of water generally allowed in oil carried by a pipeline is 0.5% of the gross volume of the oil. In the event such a percentage is exceeded, the producer may be refused access to the pipeline or penalised accordingly.

Similarly, oil producers have reasons for ensuring they too have information concerning the water content of the oil which they have produced. First, they may wish to corroborate the water content figures obtained by the pipeline operator. Second, they may wish to monitor performance of their water removal equipment and, third, they may wish to optimize their water removal processes and equipment so that they meet the standards required by the pipeline operator but do not substantially exceed them which can be more profitable for their operations.

Several previous instruments have been used to measure the water content of a liquid hydrocarbon and water mixture but each suffers from various disadvantages. Such instruments include the net oil coriolis meter type instrument which does not have sufficient accuracy for measuring small amounts of water because it depends on the accuracy of mass, density and temperature measurements. It likewise depends on the hydrocarbon and water densities remaining constant during operation and that such densities be established prior to the initiation of operation of the device. The errors in the readings obtained by net oil coriolis meter devices can be in the order of 0.5% water, which errors are in the range or even greater than the amount of water in the oil-water mixture which is permitted by the pipeline operator.

Further instruments used in the measurement of water content in an oil-water mixture include the cut monitor or basal sediment and water ("BS & W") type instrument which utilises capacitance to determine the volume of water in the oil. Such instruments are far more accurate than the coriolis type instruments for measuring small percentages of water but they too depend on the density of the hydrocarbon mixture and temperature remaining constant although some such instruments do utilise temperature compensation.

Manual sampling is also used but it suffers from clear disadvantages, perhaps the greatest of which is that it is not a continuous sampling on-line technique. Automatic sampling gives an average rather than an instantaneous water cut. Both manual and automatic sampling require that the sample obtained of the oil and water mixture be a representative sample.

Instruments known as temperature compensated basal sediment and water ("BS & W") monitors are also utilised. A resistance temperature device ("RTD") is used with the BS & W instrument. The RTD is inserted in and measures the temperature of the fluid stream. It calculates the corrected water content using a linear relationship between the temperature and the dielectric constant of the oil. In addition to the measurement of the water content for a mixture of specific density, the instrument allows four(4) different mixture densities to be measured by utilising a linear relationship between the capacitance and the water content. However, it also suffers limitations in that the density of the mixture must be known prior to the startup of the apparatus and it is assumed that the density is constant over time which may not be correct. The four(4) densities must be close to each other for good accuracy and an external switch is required to select the calibrated density closest to that of the mixture being tested. However, errors still arise when the density of the mixture differs from the densities for which the apparatus is calibrated.

To improve the correlation between the capacitance measurement of the liquid hydrocarbon and water mixture obtained by the BS & W monitor and the corresponding value for water content percentage of the mixture being measured, it is noted that errors can arise. For example, if the liquid hydrocarbon and water mixture is inserted into a capacitance measuring device and the capacitance measurement obtained is "Y1", the percentage water content of the mixture "X1" is directly obtained from the linear relationship shown therein.

Figure 3:
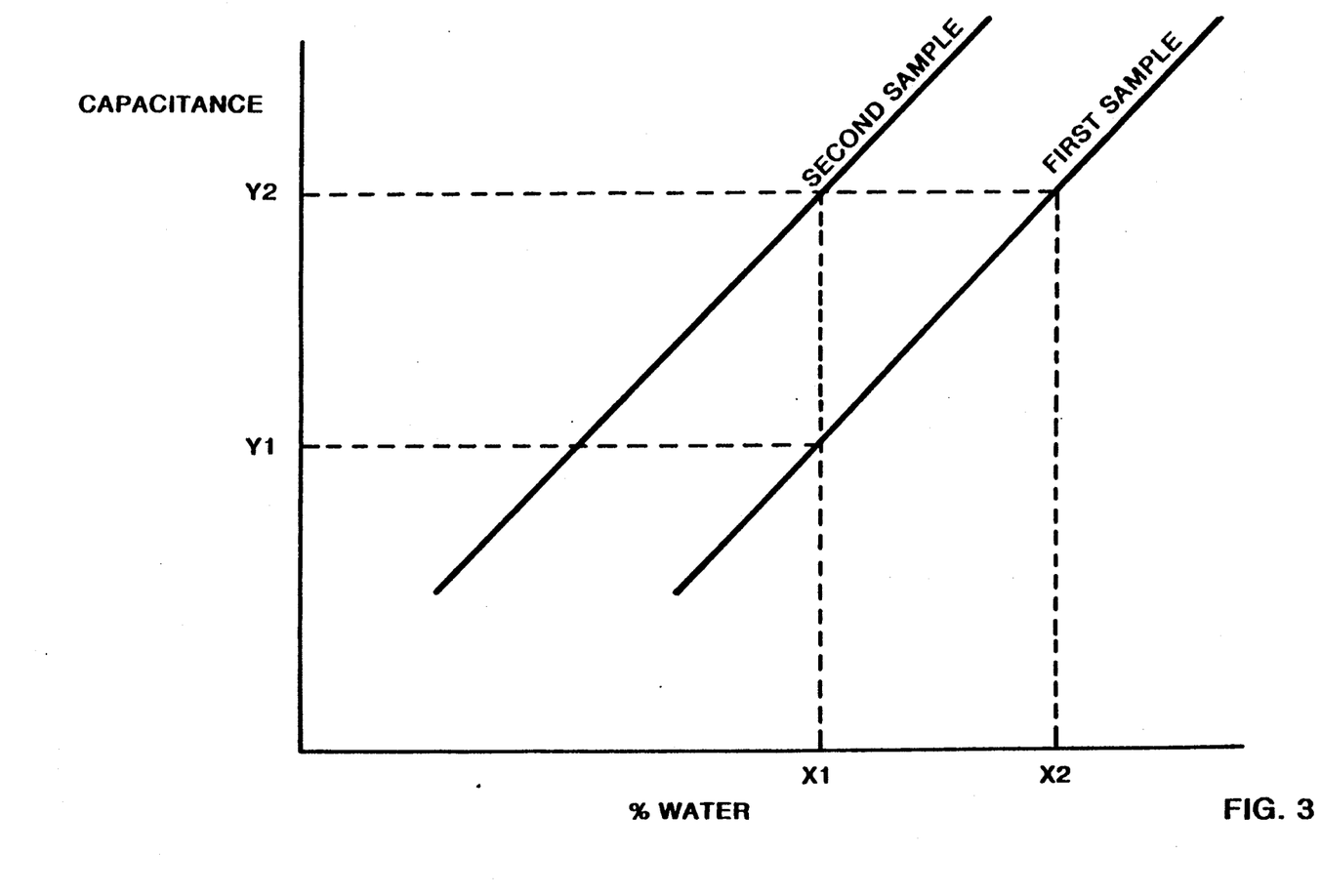
FIG. 3 is a diagram illustrating the capacitance of a liquid hydrocarbon and water mixture for a first and second sample.

However, if the density of a second sample of liquid hydrocarbon changes from the density of the first sample of liquid hydrocarbon being measured with reference to FIG. 3 as would be the case, for example, where oil from a different field is being sampled and even though the water content may be precisely the same in the second sample, the capacitance can and will change to, say, "Y2". Correlating the capacitance value of "Y2" to the water content value will give an erroneous reading of "X2".

Techniques have been adapted in an attempt to minimize the erroneous readings. For example, different sets for capacitance tables can be generated depending on the density of the liquid hydrocarbon intended to be carried. Again with reference to FIG. 3, a second sample of known density will result in a capacitance reading of "Y2" and in correlating this value to water content, it will be found that the correct value of "x1" will be obtained assuming that the two samples are as described above; that is, that the two samples have the same water content. This technique, however, is clearly disadvantageous when the density of the liquid hydrocarbon-water mixture changes unbeknownst to the operators.

In capacitance type instruments such as cut monitor instruments, three variables effect the capacitance reading, namely the area of the plates between which the capacitance is taken, the distance between the plates and the dielectric constant of the material between, the plates. Since the area of the plates and the distance between them can be held constant by the layout of the instrumentation, the only remaining factor affecting capacitance is the dielectric constant of the material being measured between the plates.

The dielectric constant for petroleum changes depending upon the density of the oil and the temperature of the oil. As the density of the oil increases, the dielectric constant increases and as the density decreases, the dielectric constant decreases. Likewise, as the temperature of the oil increases, the density decreases and the dielectric constant therefore decreases.

Since the dielectric constant for oil is approximately 2.0, depending upon its density and the dielectric constant for water is approximately 80, as the water content of the oil increases, the dielectric constant will also increase.

However, while some previous instruments have provided compensation for dielectric changes due to temperature changes and while some instruments have provided for manual calibration of the instrument depending on the density of the oil and water mixture carried by the pipeline, none have provided on-line compensation for dielectric changes due to density changes in the oil-water mixture which results by differing oil compositions. This is clearly disadvantageous since the product being carried by the pipeline may change significantly over time thereby resulting in incorrect readings for the water content of the oil.

A further problem which produced incorrect readings for the instrument resulted from the previously incorrect understanding that the capacitance of the oil was directly proportional to the density. In fact, it has been found that the relationship is non-linear with the result that the oil dielectric constant can be more accurately determined than previously.

Yet a further problem is set forth herein to assist a full understanding of the invention. This problem relates to the dual effect of dielectric constant changes due to changes in density and temperature. It was previously thought that two compensations were needed to obtain capacitance, namely that compensation due to temperature change and that compensation due to density change. However, it has been found that temperature compensation need not be performed for the instrument of the present invention. Rather, as the density changes in the oil-water mixture and as the dielectric constant likewise changes as a result of such density changes, it appears that temperature compensation itself need not be performed. It is emphasized that, at the present time, not enough is known about this phenomena to ensure that the statements made herein are correct without qualification but, based upon results to date, it does appear as if such temperature compensation need not be made.

SUMMARY OF THE INVENTION

According to one aspect of the invention, there is provided apparatus for determining the water content of a liquid hydrocarbon and water mixture comprising means to measure the density of said liquid hydrocarbon and water mixture, means to correlate said density measurement of said liquid hydrocarbon and water mixture to a first dielectric constant for said liquid hydrocarbon, means to measure the capacitance of said liquid hydrocarbon and water mixture and to convert said capacitance to a second dielectric constant of said liquid hydrocarbon and water mixture, means to obtain the difference between said first and second dielectric constants and means to convert said difference between said dielectric constants to a reading indicating the water content of said liquid hydrocarbon and water mixture.

According to a further aspect of the invention, there is provided a method of measuring the water content of a liquid hydrocarbon and water mixture comprising the steps of determining the density of said liquid hydrocarbon and water mixture, converting said density determination to a first dielectric constant for said liquid hydrocarbon, determining the capacitance of said liquid hydrocarbon and water mixture, converting said capacitance to a second dielectric constant for said liquid hydrocarbon and water mixture, measuring the difference between said first and second dielectric constants and converting said difference to a value for the water content of said liquid hydrocarbon and water mixture.

BRIEF DESCRIPTION OF THE SEVERAL VIEWS OF THE DRAWINGS

A specific embodiment of the invention will now be described, by way of example only, with the use of drawings in which.

DESCRIPTION OF SPECIFIC EMBODIMENT

Figure 1:
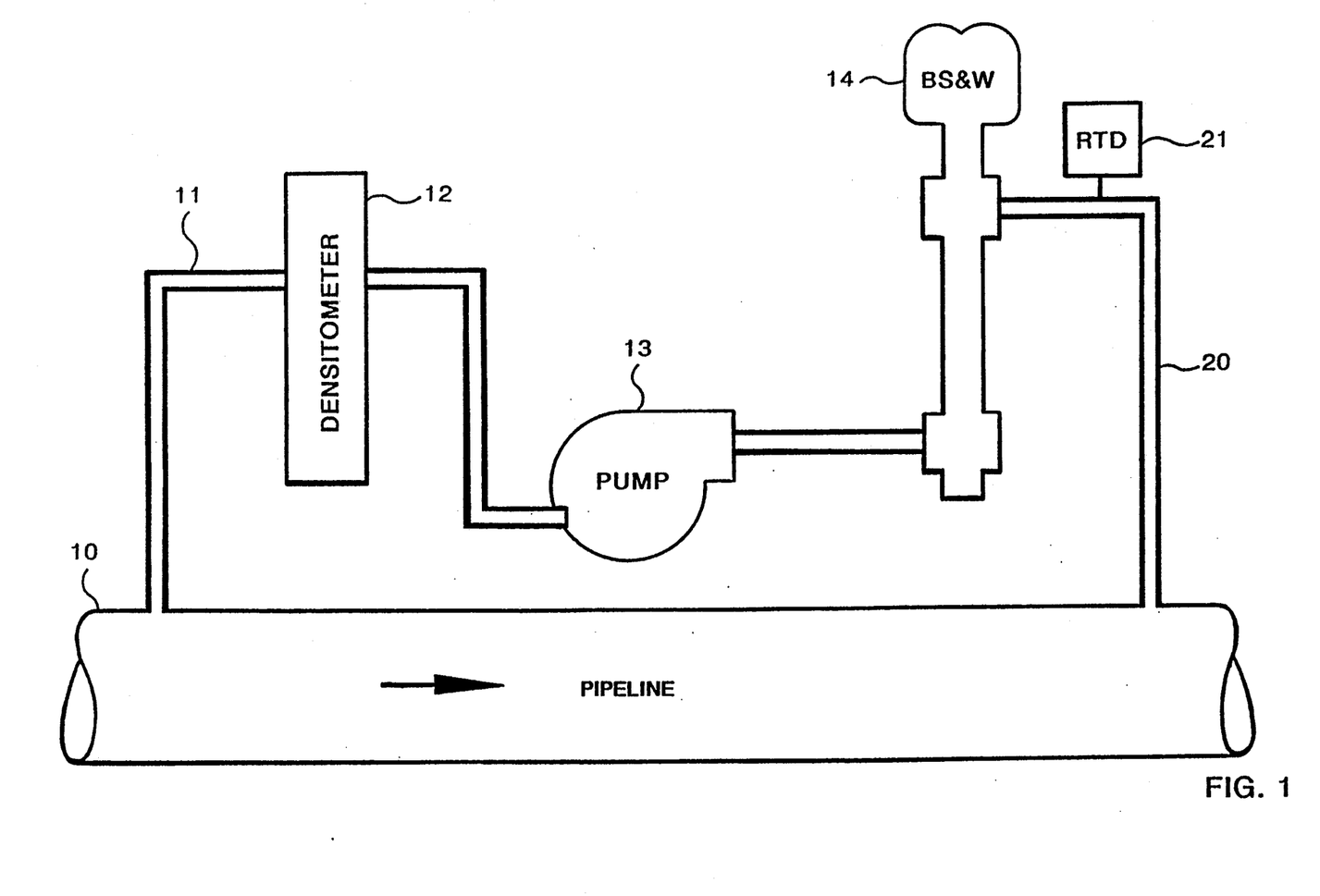
FIG. 1 is a view of the apparatus according to the invention in its operating relationship with the pipeline being monitored.

Reference is made to the drawings and, in particular to FIG. 1 which illustrates a pipeline 10 with a liquid hydrocarbon, conveniently oil, flowing therein. A branch line 11 extends from the pipeline 10 and a densitometer 12 is connected to the branch line 11. A pump 13 is connected downstream from the densitometer 12 and a basal sediment and water ("BS & W")instrument 14 is mounted downstream of pump 13 and acts to measure the capacitance of the oil and water mixture flowing therethrough. The BS & W instrument 14 returns the oil and water mixture to the pipeline 10 by way of return line 20. A resistance temperature device ("RTD") 21 may be utilised to measure the temperature of the oil and water mixture passing through the BS and W instrument 14 if desired or necessary.

OPERATION

Figure 2:
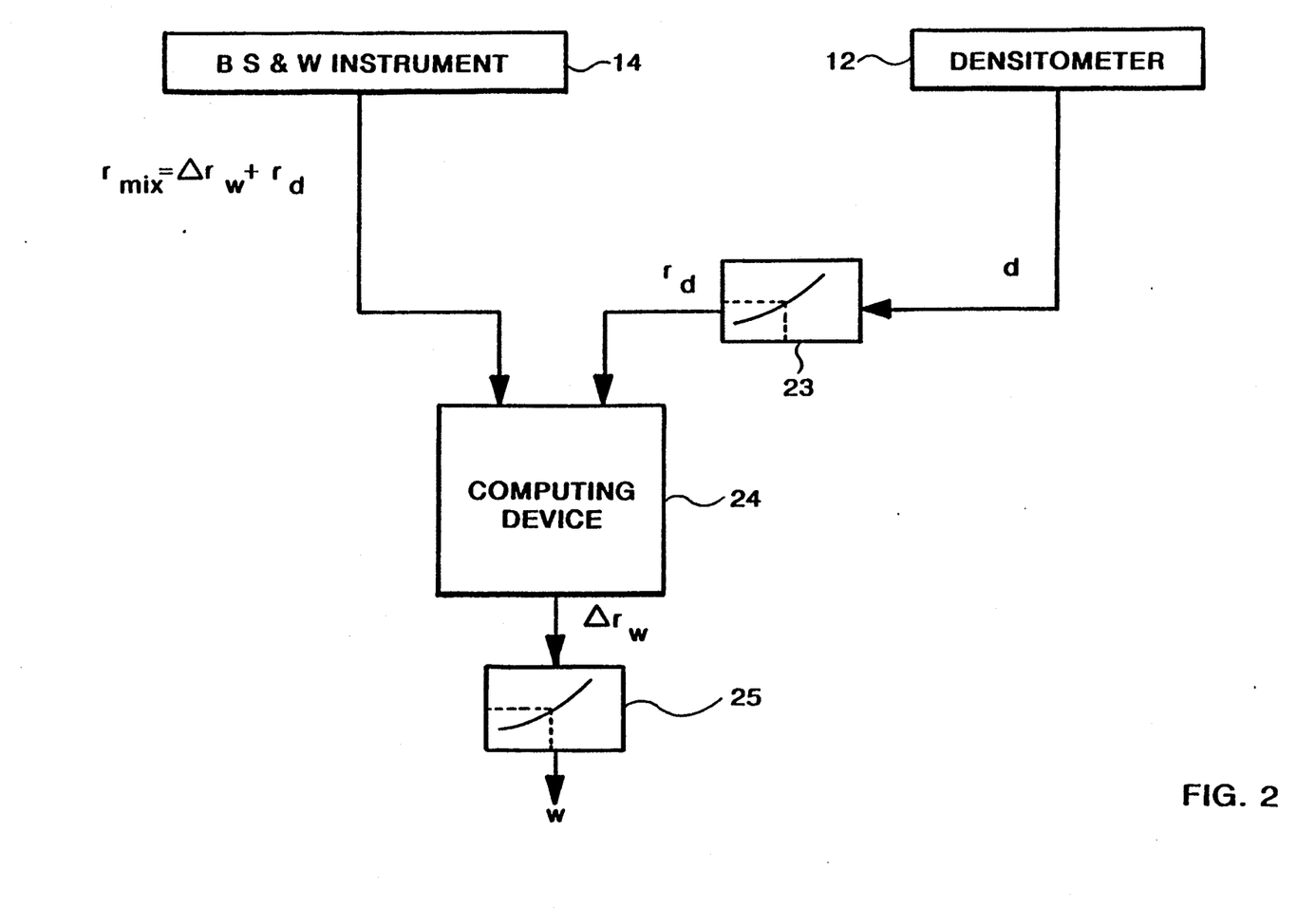
FIG. 2 is a diagrammatic schematic view of the operation of the water cut monitor according to the invention.

In operation and with reference to FIGS. 1 and 2, an oil and water mixture will generally enter the densitometer 12 from pipeline 10 through branch line 11. The densitometer 12 will measure the density of the oil and water mixture and this result, say d, will then be correlated with the corresponding value of dielectric constant, say rd, by the use of the experimentally generated data illustrated in FIG. 4. It will be noticed that while previously, it was thought that the relationship between the density of the mixture and the dielectric constant was linear; that is, a straight line as opposed to the "two-stage" linear relationship illustrated in FIG. 4, empirical data suggest this is not the case and, indeed, that considerable error can arise if a linear relationship is assumed. It will also be noted that the chart of FIG. 4 correlates the density with the dielectric constant for dry oil; that is, for oil without measurable water content. While this does introduce a small error as will be shown in greater detail hereafter, it has been assumed that the density does not significantly differ with or without water in the mixture and that, accordingly, that the value obtained for rd is appropriate for the applications under which the instrument is intended to be used and, in fact, this has been shown to be correct.

The water and oil mixture from densitometer 12 is then moved downstream by the use of pump 13 and into the BS and W instrument 14 where the capacitance of the oil and water mixture is measured in the normal way and a value for the dielectric, $r_{mix}$, is obtained. The value for $r_{mix}$ has been found to be the sum of the dielectric of the oil, $r_d$ plus an additional amount, $\Delta r_w$, due to the contribution of the water content as expressed below:

$$r_{mix} = r_d + \Delta r_w \text{ and, therefore,}$$

$$\Delta r_w = r_{mix} - r_d$$

Figure 4:
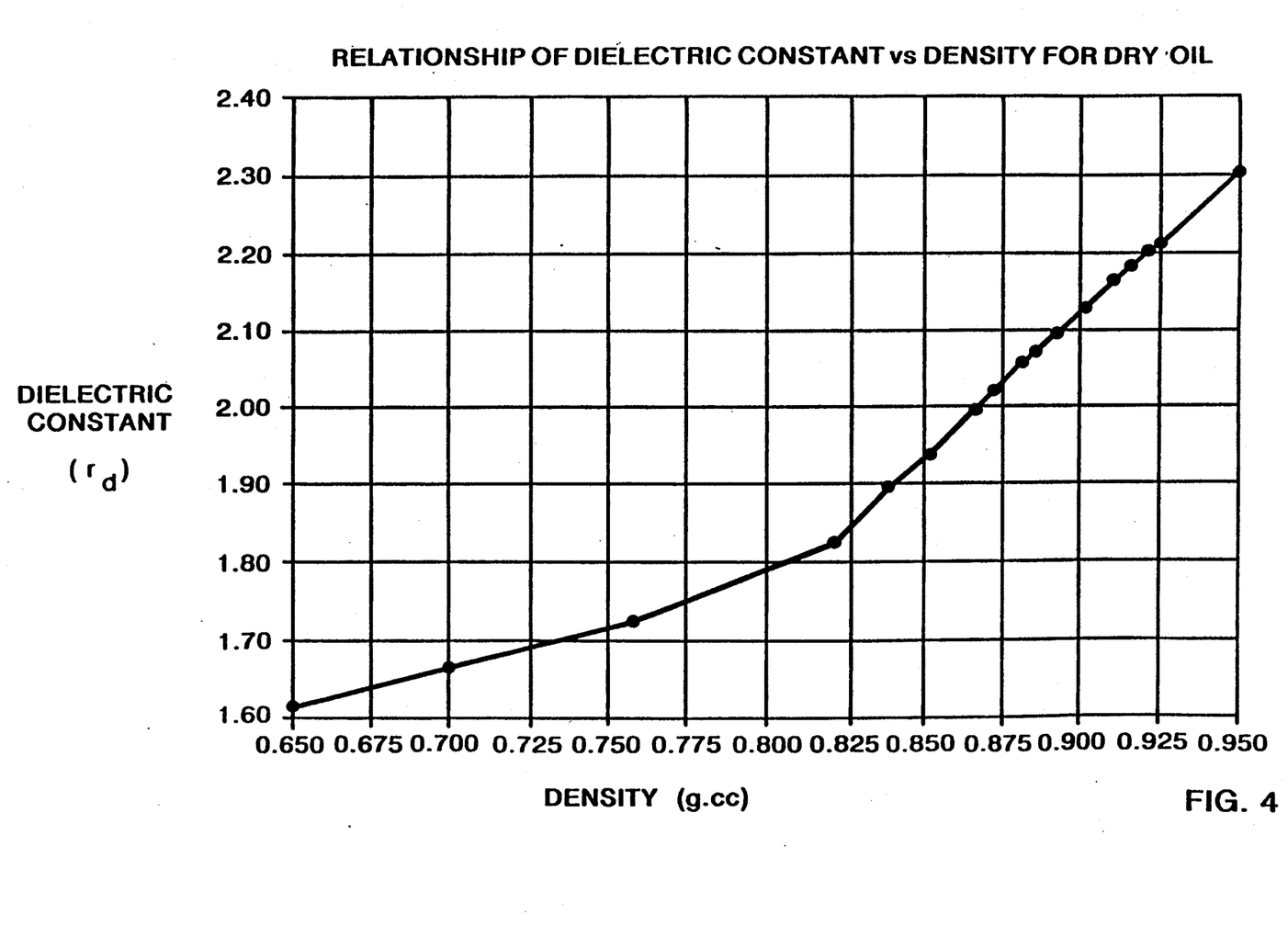
FIG. 4 is a non-linear curve obtained experimentally and cross-referencing the dielectric constant against the density of dry oil measured by the densitometer.

Since the value for rd is known from reading the density "d" from densitometer 12 and correlating the density reading to a value for the dielectric constant rd by utilising FIG. 4 through linearization device 23, the difference between the two measurements is obtained within computing device 24 which provides a final value for change in dielectric $\Delta r_w$ which is due to the water content of the oil and water mixture. This value is then correlated through the use of FIG. 5 utilizing linearization device 23, to obtain the percentage water content of the oil and water mixture by volume and may be displayed or recorded as desired by the operator.

In the event the densitometer 12 measures the density and temperature of the mixture passing therethrough, and from these measurements internally calculates a compensated density at a specified reference temperature, the BS & W monitor 14 will also need to be temperature compensated. For this purpose, a resistance temperature device 21 will also be provided to take the temperature of the fluid stream from the BS & W monitor 14. Temperature compensation utilizing the RTD 21 may be switched on and off depending upon whether it is to be used or not.

It will be noted that there is an error introduced in the measuring process described by the use of the data appearing on FIG. 4 which correlates the density reading of dry oil against its dielectric constant. However, it has also been found that the error at low concentrations of water is insignificant.

For example, and with reference to FIG. 2, it will be assumed that the density of the oil in the oil water mixture being measured by the densitometer 12 is 0.8 g/cc and that the density of the water in the oil water mixture being measured by the densitometer 12 is 1.0 g/cc. It is assumed that the density of the oil-water mixture does not change significantly from the density of dry oil and, accordingly, the densitometer should measure the density of the oil-water mixture at approximately 0.8. With reference now to FIG. 4, it will be seen that a value for the density of 0.8 on the abscissa of FIG. 4 correlates to a dielectric constant, $r_d$, of approximately 1.79. This value for $r_d$, therefore, Will be entered into the computing device 13.

Meanwhile, the dielectric constant of the oil water mixture will also be measured by the BS & W instrument 14 and this measurement is assumed to be for the purposes of this example to be 1.83. The value of 1.83 is then taken to be the value for $r_{mix}$ and by the use of the equation, $\Delta = r_{mix} - r_d$, the value for $\Delta r_w$ is obtained as follows:

$$\Delta r_w = 1.83 - 1.79 = 0.04$$

Figure 5:
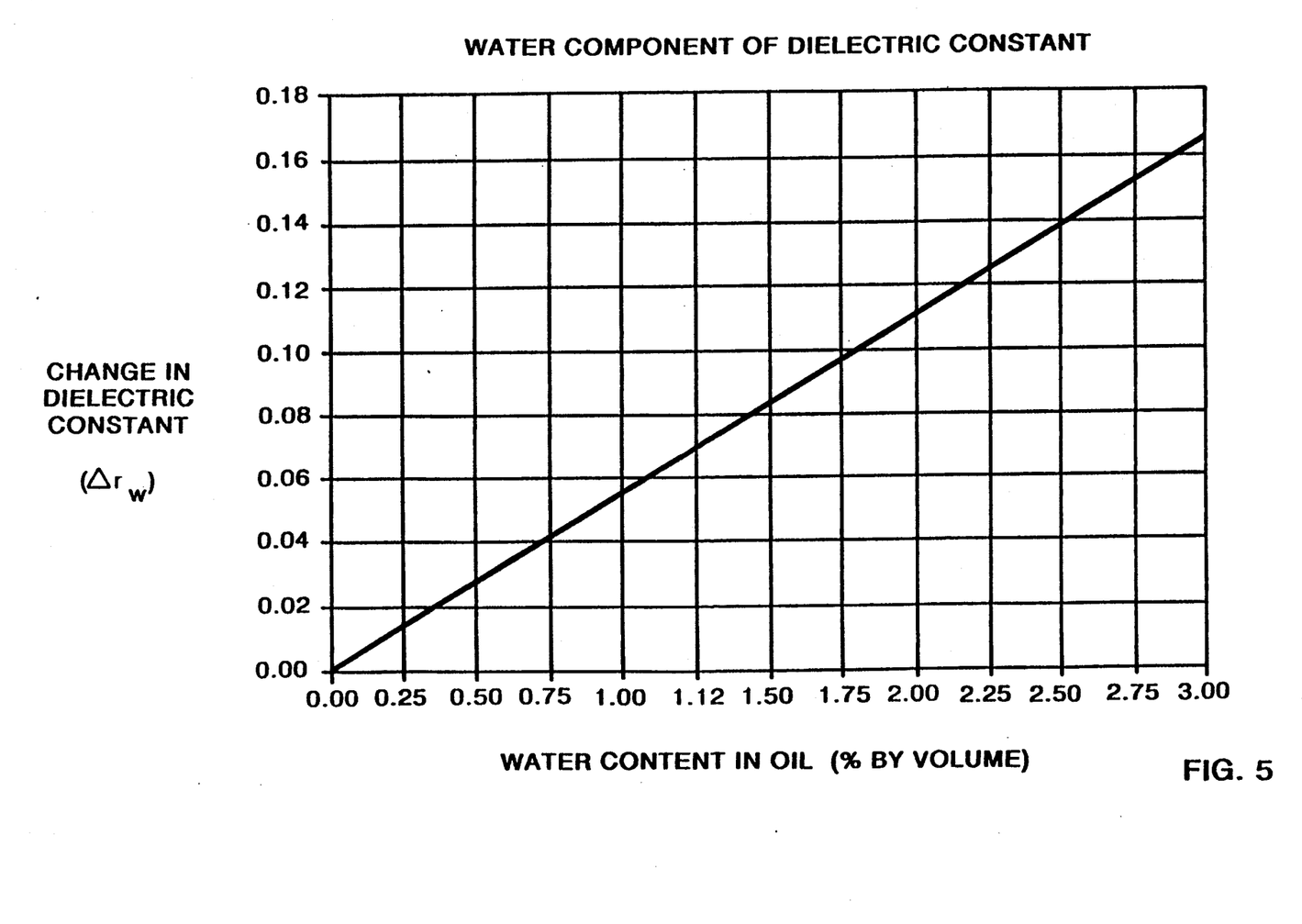
FIG. 5 is a cross-reference chart which correlates the change in dielectric constant to the actual water content of the oil.

The value of the dielectric of 0.04 is correlated to water content through the use of FIG. 5 thereby obtaining a value of water content of approximately 0.72% water by volume.

It will be assumed that the density of the mixture $d_{mix}$ can be computed as follows:

$$d_{mix} = \text{(percent oil) (oil density)} + \\ \text{(percent water) (water density)} = \\ (100\% - 0.72\%)(0.8) + (0.72\%)(1.00) = .8014$$

Thus, there is a slight error that does arise but the assumption that the change is small is a valid one.

Figure 6:
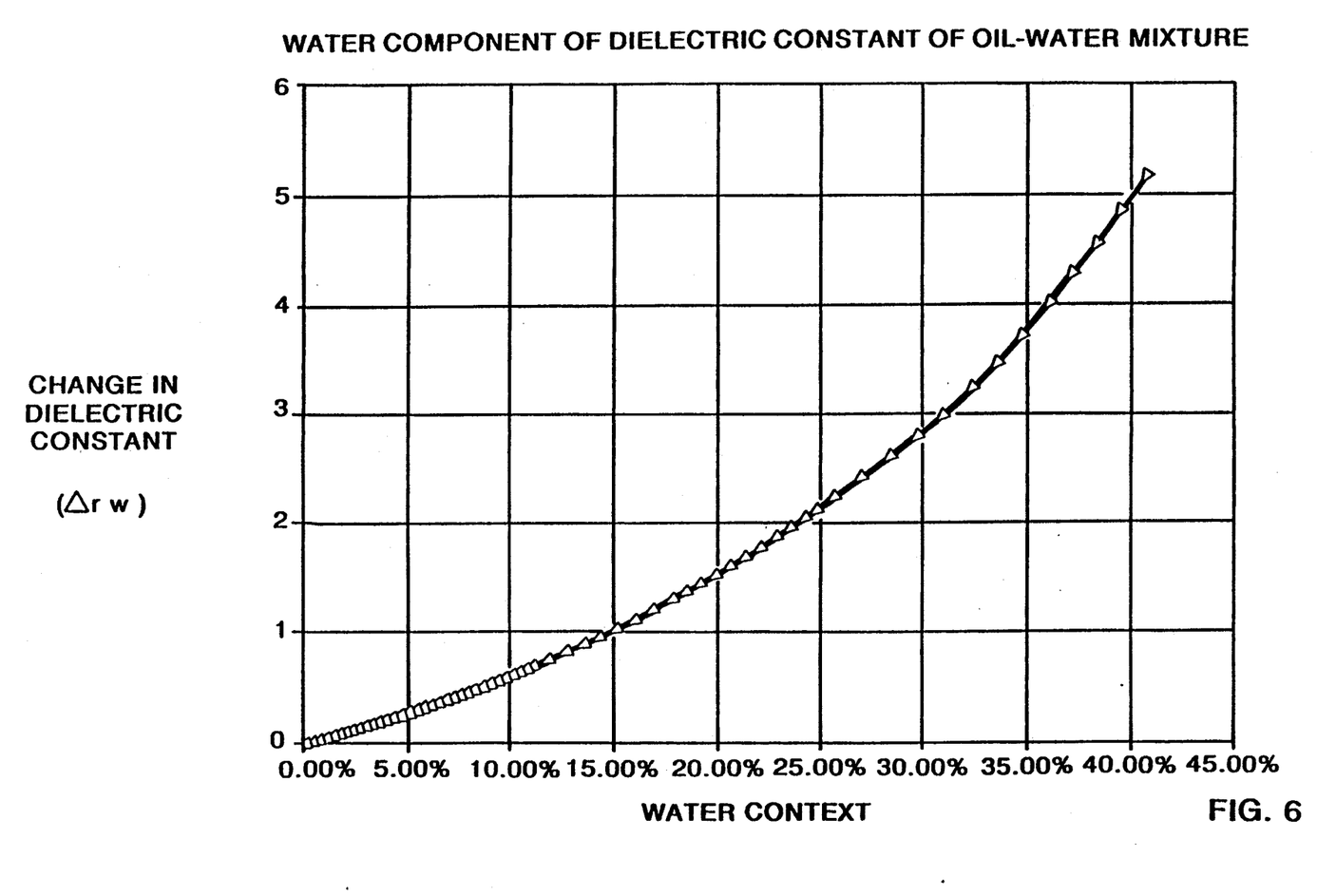
FIG. 6 is a non-linear curve obtained experimentally which correlates the change in dielectric constant to the actual water content of the oil for high percentages of water in the oil.

It will be further noted that there is an error introduced in the measuring process by use of the correlation appearing on FIG. 5 which correlates linearly the water component of the dielectric of the mixture, $\Delta r_w$ against its water content. It is known that this relationship is non-linear and exponential in nature as illustrated in FIG. 6. However, it has been found that the error at low concentrations of water is insignificant.

While a specific embodiment of the invention has been described, many modifications will readily occur to those skilled in the art to which the invention relates and such description should be taken as illustrative of the invention only and not as limiting its scope as defined in accordance with the accompanying claims.

What is claimed is:

1. Apparatus for determining the water content of a liquid hydrocarbon and water mixture having liquid hydrocarbons of varying densities comprising means to measure the density of said liquid hydrocarbon and water mixture, means for obtaining a first dielectric constant for said liquid hydrocarbon from the non-linear relationship between said first dielectric constant and said density of said liquid hydrocarbon and water mixture, means for measuring the value of the capacitance of said liquid hydrocarbon and water mixture, means for obtaining a second dielectric constant of said liquid hydrocarbon and water mixture from the value of said capacitance, means for obtaining the difference between said first and second dielectric constants and means for converting said difference between said first and second dielectric constants to a reading indicating the water content of said liquid hydrocarbon and water mixture.

2. Apparatus as in claim 1 wherein said density measuring means is a densitometer.

3. Apparatus as in claim 1 wherein said density measuring means is a basal sediment and water monitor.

4. Apparatus as in claim 3 wherein said liquid hydrocarbon is oil.

5. A method of measuring the water content of a liquid hydrocarbon and water mixture having hydrocarbons of varying densities comprising the steps of obtaining the density of said liquid hydrocarbon and water mixture, obtaining a first dielectric constant for said liquid hydrocarbon from the non-linear relationship between said first dielectric constant and said density of said liquid hydrocarbon and water mixture, determining the capacitance of said liquid hydrocarbon and water mixture, obtaining a second dielectric constant for said liquid hydrocarbon and water mixture from said capacitance, measuring the difference between said first and second dielectric constants and converting said difference to a value for the water content of said liquid hydrocarbon and water mixture.

* * * * *